United States Patent
Sobek

(10) Patent No.: US 10,947,578 B2
(45) Date of Patent: Mar. 16, 2021

(54) BIOLOGICAL AIR SAMPLING DEVICE

(71) Applicant: Edward Sobek, Oak Ridge, TN (US)

(72) Inventor: Edward Sobek, Oak Ridge, TN (US)

( * ) Notice: Subject to any disclaimer, the term of this patent is extended or adjusted under 35 U.S.C. 154(b) by 459 days.

(21) Appl. No.: 15/491,410

(22) Filed: Apr. 19, 2017

(65) Prior Publication Data
US 2018/0306679 A1  Oct. 25, 2018

(51) Int. Cl.
*G01N 1/22* (2006.01)
*C12Q 1/24* (2006.01)
*G01N 1/24* (2006.01)

(52) U.S. Cl.
CPC ............. *C12Q 1/24* (2013.01); *G01N 1/2214* (2013.01); *G01N 2001/2223* (2013.01); *G01N 2001/245* (2013.01)

(58) Field of Classification Search
CPC ............... G01N 1/2214; G01N 1/2273; G01N 2001/2223; G01N 1/2205
See application file for complete search history.

(56) References Cited

U.S. PATENT DOCUMENTS

| | | | |
|---|---|---|---|
| 6,087,183 A | 7/2000 | Zaromb | |
| 6,463,815 B1 | 10/2002 | Tallentire et al. | |
| 6,769,316 B2 | 8/2004 | Rogers et al. | |
| 6,867,413 B2 | 3/2005 | Basch et al. | |
| 6,898,990 B2 | 5/2005 | Rogers et al. | |
| 6,985,818 B1 | 1/2006 | Samuels | |
| 7,195,899 B1 | 3/2007 | Chin et al. | |
| 7,326,387 B2 | 2/2008 | Arts et al. | |
| 2003/0124027 A1 | 7/2003 | Swider | |
| 2004/0047776 A1 | 3/2004 | Thomsen | |
| 2006/0117872 A1 | 6/2006 | Basch et al. | |
| 2013/0273520 A1* | 10/2013 | Sobek | G01N 1/2273 435/5 |
| 2016/0032352 A1 | 2/2016 | Sobek | |
| 2016/0231205 A1 | 8/2016 | David | |

FOREIGN PATENT DOCUMENTS

| | | |
|---|---|---|
| GB | 2064787 A | 6/1981 |
| GB | 2510501 A | 6/2014 |
| WO | 2015138681 A1 | 9/2015 |

* cited by examiner

*Primary Examiner* — Jill A Warden
*Assistant Examiner* — Dwayne K Handy
(74) *Attorney, Agent, or Firm* — Luedeka Neely Group, P.C.

(57) ABSTRACT

An air sampling device is disclosed which includes one or more air sampling cassettes, with each cassette having a cassette internal diameter and a sample collection media disposed within the cassette internal diameter. The sum of the interior diameters of the air sampling cassettes is from about 2.5 mm to about 65 mm. The device also includes a sampling device casing having one or more air inlet orifices, an air outlet orifice, and an interior passageway in flow communication with both air inlet orifices and the air outlet orifice. One air sampling cassette is attached to each air inlet orifice. The device also includes a fan for drawing air through the air sampling cassettes and the interior passageway at an air flow rate. The device produces a noise level of less than 40 dBA, measured at a distance of 1 foot from the air outlet orifice, when the air flow rate is from about 0.5 to about 2.0 liters per minute. A method for air sampling is also disclosed.

22 Claims, 3 Drawing Sheets

BIOLOGICAL AIR SAMPLING DEVICE

FIELD

This disclosure relates to air sampling devices and methods. More particularly, this disclosure relates biological air sampling devices and methods having a reduced noise emissions level.

BACKGROUND

Modern hospitals and other health care facilities offer a wide variety of advanced and beneficial treatments to injured and infirmed patients. Unfortunately, however, the high concentration of elderly, infirmed, and often immuno-compromised patients in hospitals and other health care facilities also creates the potential for the rapid transmission of infectious diseases. In such environments, it may be desirable to periodically or continuously collect and analyze air samples in order to detect the presence of airborne biological contaminants. This is particularly desirable in intensive care and critical care facilities housing the most infirmed patients.

The use of conventional air sampling equipment in such environments, however, is problematic because air sampling devices are typically large in size and noisy in operation. The size of such air sampling devices make them cumbersome to install within the relatively small confines of hospital rooms. Moreover, the high noise levels emitted by conventional air sampling equipment are disruptive to patient rest, thus making their usage impractical or even counterproductive in hospital rooms.

Consequently, it is desirable to provide a compact air sampling device for use in hospitals and other health care facilities. Further if would be particularly desirable if the air sampling device operated at noise emission levels which are substantially lower than conventional air sampling devices—at noise levels which would not be disruptive to the rest of patients in the hospital.

SUMMARY OF THE INVENTION

The above and other needs are met by an air sampling device according to the current disclosure. According to one embodiment, the air sampling device includes one or more air sampling cassettes, with each cassette having a sampling cassette internal diameter and a sample collection media disposed within the cassette internal diameter. The sum of the interior diameters of the air sampling cassettes is from about 2.5 mm to about 65 mm. The device also includes a sampling device casing having one or more air inlet orifices, an air outlet orifice, and an interior passageway in flow communication with both air inlet orifices and the air outlet orifice. One air sampling cassette is attached to each air inlet orifice. The device also includes a fan disposed within the casing interior passageway for drawing air through the air sampling cassettes and the interior passageway at an air flow rate.

In operation, the air sampling device produces a noise level of less than 40 dBA, measured at a distance of 1 foot from the air outlet orifice, when the air flow rate is from about 0.5 to about 2.0 liters per minute.

In another aspect, the present disclosure provides a method for collecting biological air contaminant samples. According to one embodiment, the method includes a first step of attaching one or more air sampling cassettes to one or more air inlet orifices of an air sampling device.

Each of the aforementioned sampling cassettes has a sampling cassette internal diameter and a sample collection media disposed within the cassette internal diameter. Moreover, the sum of the interior diameters of the air sampling cassettes is from about 2.5 mm to about 65 mm. Additionally, the air sampling device includes a casing having the one or more air inlet orifices, an air outlet orifice, and an interior passageway in flow communication with both the air inlet orifices and the air outlet orifices. A fan is also disposed within the casing interior passageway.

According to the method, air is drawn through the one or more air sampling cassettes at an air flow rate from about 0.5 to about 2.0 liters per minute, and biological air contaminants are collected on the sample collection media. The one or more air sampling cassettes are then removed from the one or more air inlet orifices.

According to the method, the air sampling device produces a noise level of less than 40 dBA, measured at a distance of 1 foot from the air outlet orifice, when the air flow rate is from about 0.5 to about 2.0 liters per minute.

The total number of air inlet orifices and air sampling cassettes may vary in different embodiments. In some instances, the sampling device preferably includes two air inlet orifices and two air sampling cassettes disposed within the air inlet orifices. In other instances, the sampling device preferably includes only one air inlet orifice and one air sampling cassette disposed within the air inlet orifice. In some embodiments, the sum of the interior diameters of the air sampling cassettes is preferably from about 8 mm to about 20 mm.

In certain embodiments according to the present disclosure, the air flow rate through the air sampling device is preferably from about 1.0 to about 1.5 liters per minute.

In some embodiments according to the present disclosure, the fan preferably rotates at a speed from about 3000 to about 5000 rpm when the air flow rate is from about 0.5 to about 2.0 liters per minute.

In general, the air sampling device of the present disclosure is quieter than conventional air sampling devices. In certain embodiments, the air sampling device preferably produces a noise level of less than 30 dBA, measured at a distance of 1 foot from the air outlet orifice, when the air flow rate is from about 0.5 to about 2.0 liters per minute. In certain embodiments, the device preferably produces a noise level of less than 40 dBA, measured at a distance of 1 inch from the air outlet orifice. In certain embodiments, the device preferably produces a noise level of less than 20 dBA, measured at a distance of 4 feet from the air outlet orifice. In certain embodiments, the device preferably produces a noise level of less than 15 dBA, measured at a distance of 6 feet from the air outlet orifice. In certain embodiments, the device preferably produces a noise level of less than 10 dBA, measured at a distance of 10 feet from the air outlet orifice. In certain embodiments, the device preferably produces a noise level of less than 40 dBA, measured at a distance of 1 inch from the air outlet orifice. In all of the foregoing measurements, the air flow rate is from about 0.5 to about 2.0 liters per minute.

In some embodiments according to the present disclosure, the sample collection media is preferably made up of polymeric fibers having a biomixture coating applied over the fibers. The biomixture coating may preferably include a mixture of a water soluble polymer, water, and at least one contaminant adherent material. The contaminant adherent material may in turn be selected from the group consisting of glycoproteins, cationic peptides and their derivatives, linear or branched synthetic polymers, polysaccharide-based delivery molecules, natural polymers, and dendrimers.

In certain embodiments according to the present disclosure, the water soluble polymer preferably includes polyvinyl alcohol.

In certain embodiments according to the present disclosure, the at least one contaminant adherent material is more preferably selected from the group consisting of fibronectin, poly-lysine, polyornithine, polybrene, polyethyleneimine, cyclodextrin, chitosan, histone, collagen, activated dendrimers, and non-activated dendrimers. Most preferably, the at least one contaminant adherent material is made up of fibronectin or poly-L-lysine.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
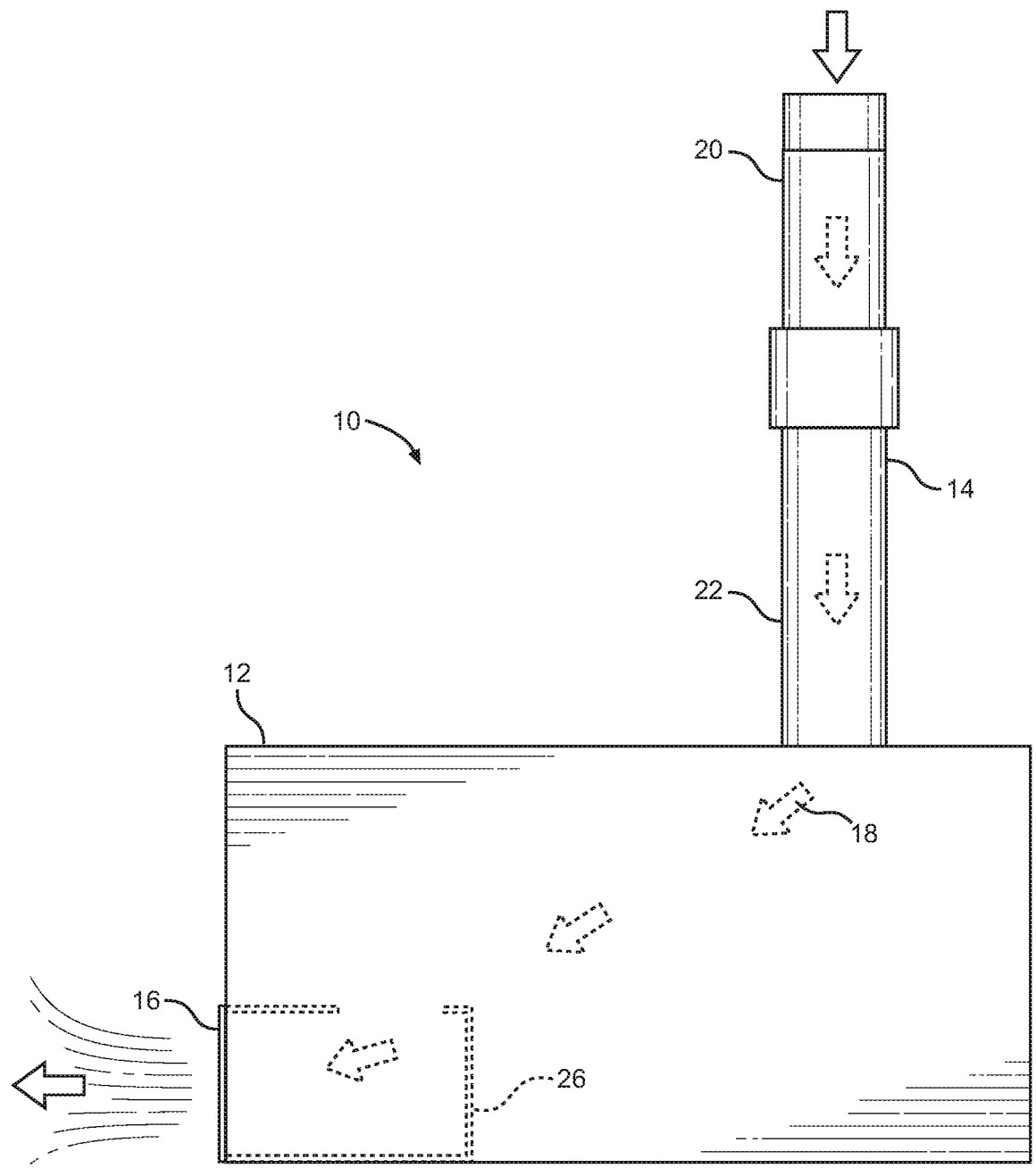
FIG. 1 is a side elevational view of an air sampling device according to one embodiment of the present disclosure.
Figure 2:
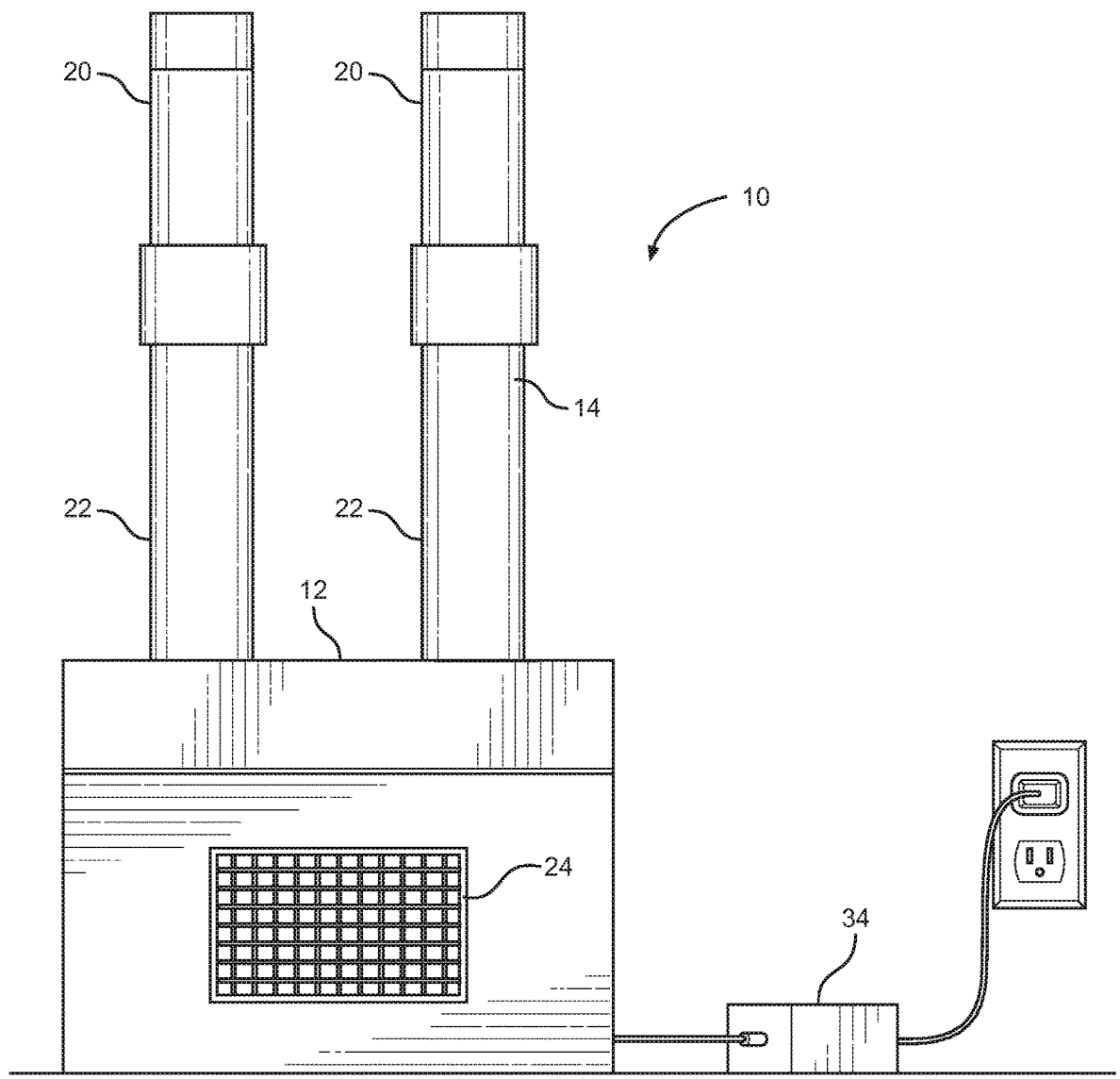
FIG. 2 is a front elevational view of an air sampling device according to one embodiment of the present disclosure.

According to the present disclosure, an air sampling device 10 is provided. As shown in FIGS. 1 & 2, the air sampling device 10 includes an outer housing or casing 12. The casing 12 may be formed from metals such as steel or from polymeric materials of suitable structural strength. The overall size of the casing 12 may vary, but typically the length of the casing 12 is from about 2 to about 5 inches and the cross-sectional area of the casing 12 is from about 4 to about 10 square inches. Thus, the overall volume of the casing 12 is typically from about 15 to about 30 cubic inches.

It may be appreciated that with these compact dimensions, the air sampling device 10 may be readily and unobtrusively installed in hospital rooms and other health care facilities. For instance, the device 10 may be mounted on the wall, on top of a table, or even behind a television set. In new healthcare facility construction, the air sampling device may also be permanently installed in preferred locations as determined by architecture design and/or and infection control professionals.

The casing 12 may also include sound insulation in order to reduce noise emissions.

The casing 12 of the air sampling device 10 casing 12 also includes one or more air inlet orifices 14, one or more air outlet orifices 16, and an interior passageway 18 in flow communication with both air inlet orifices 14 and the air outlet orifice 16. Thus, the interior passageway 18 defines the pathway for airflow within the air sampling device.

The air sampling device 10 may include one or a plurality of air inlet orifices 14. In some embodiments, the device 10 may preferably include only one air inlet orifice 14, while in other instances, the device 10 may include two air inlet orifices 14. In still other instances, the device 10 may include three, four, or more air inlet orifices 14. As discussed in more detail below, an air sampling cassette 20 is inserted or attached to each air inlet orifice 14.

As seen in FIG. 2, one or more air pipes 22 may extend outward from the casing 12 of the sampling device, with the one or more inlet orifices 14 being provided at the end of these pipes 22.

The air sampling device 10 also includes one or more air outlet orifices 16. In general, only one air outlet orifice 16 is provided, but in some instances, the device 10 may include two or more air outlet orifices 16. The air outlet orifice(s) 16 are preferably covered with a protective screen 24.

Figure 3:
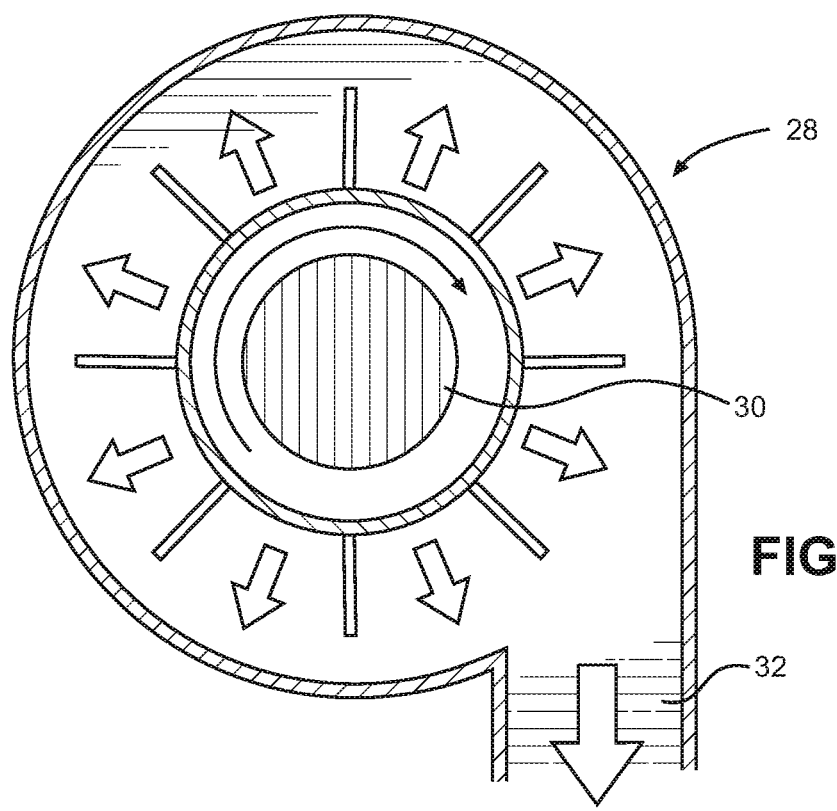
FIG. 3 is a cross-sectional plan view of a centrifugal blower according to one embodiment of the present disclosure.

Disposed within the interior passageway 18 of the air sampling device 10 is a fan 26 which is used to drawing air through the air sampling cassettes 20 and the interior passageway 18 at a desired air flow rate. The fan 26 is preferably a centrifugal blower-type fan 26. As illustrated in FIG. 3, air is pulled into the centrifugal blower 28 through a central blower opening 30. The air is then accelerated radially outward and expelled from the blower 28 via a second blower opening 32.

Electrical power is preferably supplied to the fan 26 from an external power supply 34.

In order to provide satisfactory air sampling while also providing reduced noise emissions, the fan 26 is preferably operated at a speed sufficient to provide an air flow rate through the air sampling device 10 of from about 0.5 to about 2.0 liters per minute. More preferably, the air flow rate through the air sampling device 10 is from about 1.0 to about 1.5 liters per minute. A suitably sized centrifugal blower for this purpose may be from about 0.5 to about 2 watts. At this size, the blower or other fan 26 preferably rotates at a speed from about 3000 to about 5000 rpm.

Figure 4:
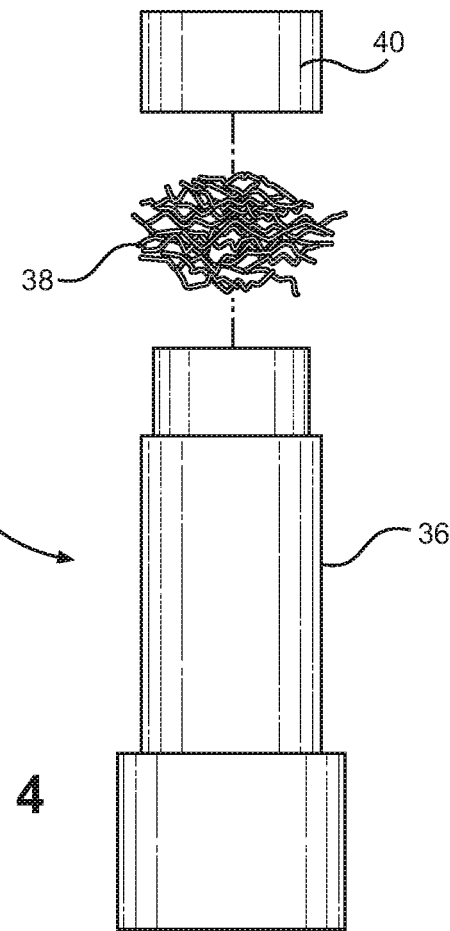
FIG. 4 is a side elevational view of an air sampling cassette according to one embodiment of the present disclosure.

The air sampling device 10 also includes one or more air sampling cassettes 20. One air sampling cassette is inserted into each air inlet orifice 14 so that the total number of air sampling cassettes 20 will equal the number of inlet orifices 14. As shown in FIG. 4, each cassette 20 includes a generally elongate tube 36 having a length of from about 3 to about 8 cm. Typically, the cassette tube 36 will have a circular or elliptical cross-section. In general, the cassette tube 36 is preferably formed from an inexpensive polymeric material such as polyethylene, polypropylene, or polyethylene terephthalate. The cassette 20 may also include a removable endcap 40, formed from similar materials.

Each air sampling cassette 20 has an internal diameter, and the internal diameter of each individual cassette 20 may vary depending upon the total number of air inlet orifices 14 and sampling cassettes 20 used in the device. Importantly, however, the inventor has discovered that the sum of all the interior diameters of the air sampling cassettes 20 is of significance in determining the final noise levels emitted from the air sampling device 10. In order to minimize noise levels from the air sampling device 10, the inventor has found that the sum of the interior diameters of the air sampling cassettes 20 is preferably from about 2.5 mm to about 65 mm. More preferably, the sum of the interior diameters of the air sampling cassettes 20 is preferably from about 20 mm to about 30 mm.

As noted above, the air sampling device 10 may include one or more air pipes 22 which extend outward from the casing 12, with the one or more inlet orifices 14 being provided at the end of these pipes 22. In such embodiments, the main diameter of the pipes 22 is preferably the same as the diameter of the air sampling cassettes 20 along most of the length of the pipe 22, with a diameter expansion at the end of the pipe 22 in order to allow the air sampling cassette 20 to slide into the inner diameter of the pipe 22.

A portion of sample collection media 38 is disposed within the internal diameter of each sampling cassette 20. In some instances, this sample collection media 38 is preferably made up of polymeric fibers having a biomixture coating applied over the fibers. The amount of sample collection media 38 within each sampling cassette 20 is typically from about 12 to about 25 milligrams.

The biomixture coating may preferably include a mixture of a water soluble polymer, water, and at least one contaminant adherent material. The amount of water soluble polymer in the mixture is preferably from about 200 parts per million ("ppm") to about 700 ppm. The amount of contaminant adherent material in the mixture is preferably from about 80 parts per billion ("ppb") to about 200 ppb.

The contaminant adherent material may typically be selected from the group consisting of glycoproteins, cationic peptides and their derivatives, linear or branched synthetic polymers, polysaccharide-based delivery molecules, natural polymers, and dendrimers. The at least one contaminant adherent material is more preferably selected from the group consisting of fibronectin, poly-lysine, polyornithine, polybrene, polyethyleneimine, cyclodextrin, chitosan, histone, collagen, activated dendrimers, and non-activated dendrimers. Most preferably, the at least one contaminant adherent material is made up of fibronectin or poly-L-lysine.

In certain embodiments according to the present disclosure, the water soluble polymer preferably includes polyvinyl alcohol.

The present disclosure also provides a method for collecting biological air contaminant samples using the air sampling device. According to this method, an air sampling device 10 as described above is located in a desired sampling area. For instance, the air sampling device 10 may be located in a hospital room or in a room in a nursing home or other extended care facility. One or more air sampling cassettes 20 are then attached to the one or more air inlet orifices 14 of the air sampling device.

The fan 26 is then started so that air is drawn through the one or more air sampling cassettes 20 at a desired air flow rate. As noted above, the air flow rate is preferably from about 0.5 to about 2.0 liters per minute. As air from the surrounding environment is drawn through the device, biological air contaminants are collected on the sample collection media 38. The air sampling device 10 may be left to operate in this capacity for a specified period of time, typically from about 7 days to about 14 days.

After this time, the fan 26 is stopped, and the one or more air sampling cassettes 20 are then removed from the one or more air inlet orifices 14. The sampling cassettes 20 may then be taken to a suitable laboratory where the sample collection media 38 is analyzed for the presence of biological contaminants.

Biological contaminants which may be identified in this manner include fungi, molds, bacteria, viruses, allergens, and toxins.

As noted above the air sampling device 10 of the present disclosure is quieter than conventional air sampling devices. In general, the air sampling device 10 produces a noise level of less than 40 dBA, measured at a distance of 1 foot from the air outlet orifice 14, when the air flow rate is from about 0.5 to about 2.0 liters per minute. More preferably, the air sampling device 10 preferably produces a noise level of less than 30 dBA, measured at a distance of 1 foot from the air outlet orifice, when the air flow rate is from about 0.5 to about 2.0 liters per minute. In fact, air sampling device 10 preferably still produces a noise level of less than 40 dBA, even when measured at a distance of only 1 inch from the air outlet orifice.

In certain embodiments, the air sampling device 10 preferably produces even lower noise levels when measured at greater distances from the air outlet orifice. In certain embodiments, the device 10 preferably produces a noise level of less than 20 dBA, measured at a distance of 4 feet from the air outlet orifice. In certain embodiments, the device 10 preferably produces a noise level of less than 15 dBA, measured at a distance of 6 feet from the air outlet orifice. In certain embodiments, the device 10 preferably produces a noise level of less than 10 dBA, measured at a distance of 10 feet from the air outlet orifice. In certain embodiments, the device 10 preferably produces a noise level of less than 40 dBA, measured at a distance of 1 inch from the air outlet orifice. In all of the foregoing measurements, the air flow rate is from about 0.5 to about 2.0 liters per minute.

With such low noise emission levels, the air sampling device 10 of the present disclosure may be advantageously used in hospitals and other health care facilities to collect air samples in order to detect the presence of airborne biological contaminants—at noise levels which would not be disruptive to the rest of patients in the hospital or other facility.

EXAMPLES

The following non-limiting examples illustrate various additional aspects of the invention. Unless otherwise indicated, temperatures are in degrees Celsius and percentages are by weight based on the dry weight of the formulation.

Example 1

Airflow Measurement Testing

A set of 24 air sampling devices made in accordance with the present disclosure were subjected to testing to determine the average air flow rate through each of the air sampling devices. Each of the devices included two air pipes extending out from the device, with each air pipe having an air inlet orifice.

Air flow measurements were obtained using a Gilian Gilibrator 2 Calibration System with an attached Standard Flow Wet Cell able to measure in the range of 20 milliliters per minute to 6 liters per minute. The Gilibrator 2 Calibration System (S/N: 1609040-S) itself was calibrated by Sensidyne, LP by instruments directly traceable to the National Institute of Standards and Technology report 8361604.

While taking the air flow measurements, the fan in each of the air sampling devices was operating at a speed of approximately 3800 rpm.

For each air sampling device, five readings were taken and averaged together to determine the average air flow rate. The air sampling device was connected to the Gilibrator via a rubber tube. The Gilibrator cell was primed by coating the inner cell wall with the supplied soap solution. Five measurements were taken with the tube connected to one of the air pipes of the air sampling device with the other air pipe being open. Thus, the measured air flow would represent only a portion (approximately one half) of the total air flow through both air pipes. The average was calculated by the Gilibrator and recorded. This is referred to as the "Dual Stack" flow measurement below.

Afterwards, the measurements on the Gilibrator were reset, and then five measurements were taken with the rubber hose attached to one of the air pipes and with the second air pipe covered and closed off. The average was again calculated by the Gilibrator and recorded. Thus, this measurement represents the entirety of the air flow through the device in this configuration. This is referred to as the "Single Stack" flow measurement.

The average measured flow rates for the Dual Stack and Single Stack configurations were as follows:

TABLE 1

Air Flow Rates

| Air Sample Device No. | Single Stack Flowrate (Liters/minute) | Dual Stack Flowrate (Liters/minute) |
|---|---|---|
| 1 | 1.21 | 0.82 |
| 2 | 1.4 | 1 |
| 3 | 1.36 | 0.97 |
| 4 | 1.26 | 0.93 |
| 5 | 1.43 | 1.09 |
| 6 | 1.25 | 0.94 |
| 7 | 1.35 | 1.12 |
| 8 | 1.35 | 1.12 |
| 9 | 1.37 | 1.09 |
| 10 | 1.36 | 1.05 |
| 11 | 1.34 | 1.14 |
| 12 | 1.3 | 1.09 |
| 13 | 1.26 | 1.03 |
| 14 | 1.26 | 1 |
| 15 | 1.31 | 0.99 |
| 16 | 1.23 | 0.97 |
| 17 | 1.44 | 1.09 |
| 18 | 1.25 | 0.94 |
| 19 | 1.29 | 1.03 |
| 20 | 1.36 | 0.99 |
| 21 | 1.27 | 1.02 |
| 22 | 1.1 | 0.87 |
| 23 | 1.33 | 1 |
| 24 | 1.22 | 0.95 |
| Average Flow Rate | 1.306 | 1.01 |

Example 2

Semi-Anechoic Chamber Sound Level Testing

Next three air sampling devices made in accordance with the present disclosure—including two devices tested for air flow rate in Example 1 above—were subjected to sound level testing to determine the noise emission levels from the device. For these tests, each of the air sampling devices was separately placed in a semi-anechoic chamber. Sound levels within the chamber were measured using a Larson Davis Model 831 sound level meter, set on z-weight and slow response.

For each air sampling device, sound levels were measured at each of the following distances from the air sampling device: (1) 4 inches (0.33 foot); (2) 1 foot; (3) 4 feet; (4) 6 feet; and (5) 10 feet. At each distance, the sound level was measured over a range of frequencies from about 31.5 Hertz to about 16,000 Hertz. These measurements were then weighted according to the standard "A" weighting curves to determine final dBA sound level which approximates the way the sound level is perceived by the human ear.

In addition, for each air sampling device, the sound level measurements were taken once with the air sampling cassette attached and a second time with the air sampling cassette removed.

While taking the sound level measurements, the fan in each of the air sampling devices was operating at a speed of approximately 3800 rpm.

The sound level measurements are summarized in the table below:

| Air Sampling Device | Sampling Cassette Attached? | Sound level (dBA) at distance from Device of: | | | | |
|---|---|---|---|---|---|---|
| | | 4 inches | 1 foot | 4 feet | 6 feet | 10 feet |
| 20 | Yes | 34.2 | 24.5 | 12.5 | 9 | 4.8 |
| 20 | No | 34.9 | 25.4 | 13.2 | 10 | 4.8 |
| 24 | Yes | 31.6 | 22.1 | 10 | 6 | 3 |
| 24 | No | 31.3 | 21.8 | 9.5 | 6 | 0 |
| 30 | Yes | 31.4 | 21.8 | 10 | 6 | 3 |
| 30 | No | 28.1 | 18.5 | 6 | 3 | 0 |
| Average | | 31.9 | 22.4 | 10.2 | 6.7 | 2.6 |

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An air sampling device comprising:
   one or more air sampling cassettes, each cassette having a sampling cassette internal diameter and a sample collection media disposed within the cassette internal diameter, wherein the sum of the interior diameters of the air sampling cassettes is from about 2.5 mm to about 65 mm;
   a sampling device casing having a cross-sectional area of less than 10 square inches, one or more air inlet orifices, an air outlet orifice, and an interior passageway in flow communication the at least one or more inlet orifices and the air outlet orifice, each air inlet orifice having an air sampling cassette attached thereto;
   a fan disposed within the casing interior passageway for drawing air through the air sampling cassettes and the interior passageway at an air flow rate;
   wherein the air sampling device produces a noise level of less than 40 dBA, measured at a distance of 1 foot from the air outlet orifice, when the air flow rate is from about 0.5 to about 2.0 liters per minute.

2. The air sampling device of claim 1, wherein the sampling device comprises two air inlet orifices and two air sampling cassettes disposed within the air inlet orifices.

3. The air sampling device of claim 1, wherein the sampling device comprises only air inlet orifice and one air sampling cassette disposed within the air inlet orifice.

4. The air sampling device of claim 1, wherein the sum of the interior diameters of the air sampling cassettes is from about 8 mm to about 20 mm.

5. The air sampling device of claim 1, wherein the air flow rate is from about 1.0 to about 1.5 liters per minute.

6. The air sampling device of claim 1, wherein the fan rotates at a speed from about 3000 to about 5000 rpm when the air flow rate is from about 0.5 to about 2.0 liters per minute.

7. The air sampling device of claim 1, wherein the air sampling device produces a noise level of less than 30 dBA, measured at a distance of 1 foot from the air outlet orifice, when the air flow rate is from about 0.5 to about 2.0 liters per minute.

8. The air sampling device of claim 1, wherein the air sampling device produces a noise level of less than 40 dBA, measured at a distance of 1 inch from the air outlet orifice, when the air flow rate is from about 0.5 to about 2.0 liters per minute.

9. The air sampling device of claim 1, wherein the air sampling device produces a noise level of less than 20 dBA, measured at a distance of 4 foot from the air outlet orifice, when the air flow rate is from about 0.5 to about 2.0 liters per minute.

10. The air sampling device of claim 1, wherein the air sampling device produces a noise level of less than 15 dBA, measured at a distance of 6 foot from the air outlet orifice, when the air flow rate is from about 0.5 to about 2.0 liters per minute.

11. The air sampling device of claim 1, wherein the air sampling device produces a noise level of less than 10 dBA, measured at a distance of 10 foot from the air outlet orifice, when the air flow rate is from about 0.5 to about 2.0 liters per minute.

12. The air sampling device of claim 1, wherein the sample collection media comprises polymeric fibers having a biomixture coating applied over the fibers.

13. The air sampling device of claim 12, wherein the biomixture coating comprises a mixture of a water soluble polymer, water, and at least one contaminant adherent material selected from the group consisting of glycoproteins, cationic peptides and their derivatives, linear or branched synthetic polymers, polysaccharide-based delivery molecules, natural polymers, and dendrimers.

14. The air sampling device of claim 13, wherein the water soluble polymer comprises polyvinyl alcohol.

15. The air sampling device of claim 13, wherein the at least one contaminant adherent material is selected from the group consisting of fibronectin, poly-lysine, polyomithine, polybrene, polyethyleneimine, cyclodextrin, chitosan, histone, collagen, activated dendrimers, and non-activated dendrimers.

16. The air sampling device of claim 14, wherein the at least one contaminant adherent material comprises fibronectin or poly-L-lysine.

17. A method for collecting biological air contaminant samples, comprising the steps of:
attaching one or more air sampling cassettes to one or more air inlet orifices of an air sampling device,
wherein each sampling cassette has a sampling cassette internal diameter and a sample collection media disposed within the cassette internal diameter and the sum of the interior diameters of the air sampling cassettes is from about 2.5 mm to about 65 mm, and
wherein the air sampling device comprises a casing having a cross-sectional area of less than 10 square inches, the one or more air inlet orifices, an air outlet orifice, and an interior passageway in flow communication with both the air inlet orifices and the air outlet orifices, and a fan disposed within the casing interior passageway;
drawing air through the one or more air sampling cassettes at an air flow rate from about 0.5 to about 2.0 liters per minute;
collecting biological air contaminants on the sample collection media; and
removing the one or more air sampling cassettes from the one or more air inlet orifices,
wherein the air sampling device produces a noise level of less than 40 dBA, measured at a distance of 1 foot from the air outlet orifice, when the air flow rate is from about 0.5 to about 2.0 liters per minute.

18. The method of claim 17, wherein the air flow rate is from about 1.0 to about 1.5 liters per minute.

19. The method of claim 17, wherein the fan rotates at a speed from about 3000 to about 5000 rpm when the air flow rate is from about 0.5 to about 2.0 liters per minute.

20. The method of claim 17, wherein the air sampling device produces a noise level of less than 30 dBA, measured at a distance of 1 foot from the air outlet orifice, when the air flow rate is from about 0.5 to about 2.0 liters per minute.

21. The method of claim 17, wherein the sample collection media comprises polymeric fibers having a biomixture coating applied over the fibers.

22. The method of claim 21, wherein the biomixture coating comprises a mixture of a water soluble polymer, water, and at least one contaminant adherent material selected from the group consisting of glycoproteins, cationic peptides and their derivatives, linear or branched synthetic polymers, polysaccharide-based delivery molecules, natural polymers, and dendrimers.

* * * * *